United States Patent
Igarashi

(10) Patent No.: US 11,876,107 B2
(45) Date of Patent: Jan. 16, 2024

(54) IMAGE PICKUP APPARATUS FOR ENDOSCOPE AND ENDOSCOPE

(71) Applicant: OLYMPUS CORPORATION, Tokyo (JP)

(72) Inventor: Takatoshi Igarashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 455 days.

(21) Appl. No.: 17/238,299

(22) Filed: Apr. 23, 2021

(65) Prior Publication Data

US 2021/0257400 A1  Aug. 19, 2021

Related U.S. Application Data

(63) Continuation of application No. PCT/JP2018/042828, filed on Nov. 20, 2018.

(51) Int. Cl.
*H01L 27/146* (2006.01)
*A61B 1/05* (2006.01)
*A61B 1/00* (2006.01)

(52) U.S. Cl.
CPC .... *H01L 27/14618* (2013.01); *A61B 1/00009* (2013.01); *A61B 1/05* (2013.01); *H01L 27/14636* (2013.01)

(58) Field of Classification Search
CPC .................................. A61B 1/05; A61B 1/051
See application file for complete search history.

(56) References Cited

U.S. PATENT DOCUMENTS

2004/0130640 A1* 7/2004 Fujimori .............. H01L 23/481
                                                         257/E31.127
2004/0245530 A1  12/2004 Kameyama et al.
(Continued)

FOREIGN PATENT DOCUMENTS

| JP | 62264659 A | * | 11/1987 |
| JP | S62-264659 A | | 11/1987 |
| JP | H02-174160 A | | 7/1990 |

(Continued)

OTHER PUBLICATIONS

International Search Report dated Feb. 19, 2019 issued in PCT/JP2018/042828.

*Primary Examiner* — Aaron B Fairchild
(74) *Attorney, Agent, or Firm* — Scully, Scott, Murphy & Presser, P.C.

(57) ABSTRACT

An image pickup apparatus for endoscope includes a resin member in which an outer dimension of a third main surface is equal to an outer dimension of a second main surface, an image pickup member having a light receiving surface smaller than the second main surface, and having a first external electrode on a back surface covered by the resin member, a fan-out wiring provided to extend between an inside and an outside of an extension space, the extension space being an extension of the image pickup member in an optical axis direction, a first through wiring penetrating through the resin member, and provided in the inside of the extension space, a first bonding electrode connected with the external electrode through the first through wiring and the fan-out wiring and forming the fan-out wiring provided on the third main surface, and an electric cable bonded to the first bonding electrode.

20 Claims, 9 Drawing Sheets

(56) References Cited

U.S. PATENT DOCUMENTS

2015/0085094 A1* 3/2015 Fujimori ............... H04N 23/52
348/294
2015/0255500 A1 9/2015 Akahoshi et al.

FOREIGN PATENT DOCUMENTS

| JP | 2004-363380 A | 12/2004 |
| JP | 2015-508299 A | 3/2015 |
| JP | 2017-103478 A | 6/2017 |
| JP | 2017-183635 A | 10/2017 |
| WO | 2014/083750 A1 | 6/2014 |
| WO | 2017/014072 A1 | 1/2017 |
| WO | 2017/057291 A1 | 4/2017 |
| WO | 2018/078765 A1 | 5/2018 |
| WO | 2018/198158 A1 | 11/2018 |
| WO | 2018/198188 A1 | 11/2018 |

\* cited by examiner

IMAGE PICKUP APPARATUS FOR ENDOSCOPE AND ENDOSCOPE

CROSS REFERENCE TO RELATED APPLICATION

This application is a continuation application of PCT/JP2018/042828 filed on Nov. 20, 2018, the entire contents of which are incorporated herein by this reference.

BACKGROUND OF THE INVENTION

1. Field of the Invention

The present invention relates to an image pickup apparatus for endoscope which includes an optical system, an image pickup member, and an electric cable, and relates to an endoscope including the image pickup apparatus for endoscope which includes the optical system, the image pickup member, and the electric cable.

2. Description of the Related Art

To shorten a distal end portion of an endoscope, an image pickup apparatus for endoscope including an ultra-small image pickup member has been developed.

International Publication No. WO 2017/014072 discloses an image pickup apparatus including bonding terminals which are provided around an image pickup device through a fan-out wiring (lead-out wiring). The fan-out wiring is provided on a resin layer which covers the image pickup device.

Compared with a plurality of external electrodes arranged on an image pickup device having a small area at short intervals (narrow pitch), a plurality of bonding electrodes are arranged on a resin layer having a large area at long intervals.

SUMMARY OF THE INVENTION

An image pickup apparatus for endoscope of an embodiment includes: an optical system including a first main surface and a second main surface on a side opposite to the first main surface; a resin member provided on the second main surface, and having a third main surface which is parallel to the second main surface, an outer dimension of the third main surface being equal to an outer dimension of the second main surface; an image pickup member including a light receiving surface and a back surface on a side opposite to the light receiving surface, the light receiving surface having a light receiving region, the light receiving surface being caused to adhere to the second main surface by a transparent resin, the back surface being covered by the resin member, the light receiving surface being smaller than the second main surface, the image pickup member including a plurality of external electrodes including a first external electrode provided on the back surface; a plurality of fan-out wirings, each of which is provided to extend between an inside part and an outside part of an extension space, the extension space being an extension of the image pickup member in an optical axis direction; a plurality of through wirings including a first through wiring penetrating through the resin member, connected with the first external electrode, and provided in the inside part of the extension space; a plurality of bonding electrodes including a first bonding electrode provided on the third main surface, connected with the first external electrode through the first through wiring, and forming a fan-out wiring of the plurality of fan-out wirings; and a plurality of electric cables bonded to the plurality of bonding electrodes.

In an endoscope including an image pickup apparatus for endoscope of an embodiment, the image pickup apparatus for endoscope includes: an optical system including a first main surface and a second main surface on a side opposite to the first main surface; a resin member provided on the second main surface, and having a third main surface which is parallel to the second main surface, an outer dimension of the third main surface being equal to an outer dimension of the second main surface; an image pickup member including a light receiving surface and a back surface on a side opposite to the light receiving surface, the light receiving surface having a light receiving region, the light receiving surface being caused to adhere to the second main surface by a transparent resin, the back surface being covered by the resin member, the light receiving surface being smaller than the second main surface, the image pickup member including a plurality of external electrodes including a first external electrode provided on the back surface; a plurality of fan-out wirings, each of which is provided to extend between an inside part and an outside part of an extension space, the extension space being an extension of the image pickup member in an optical axis direction; a plurality of through wirings including a first through wiring penetrating through the resin member, connected with the first external electrode, and provided in the inside part of the extension space; a plurality of bonding electrodes including a first bonding electrode provided on the third main surface, connected with the first external electrode through the first through wiring, and forming a fan-out wiring of the plurality of fan-out wirings; and a plurality of electric cables bonded to the plurality of bonding electrodes.

DETAILED DESCRIPTION OF THE PREFERRED EMBODIMENT

<Endoscope>

Figure 1:
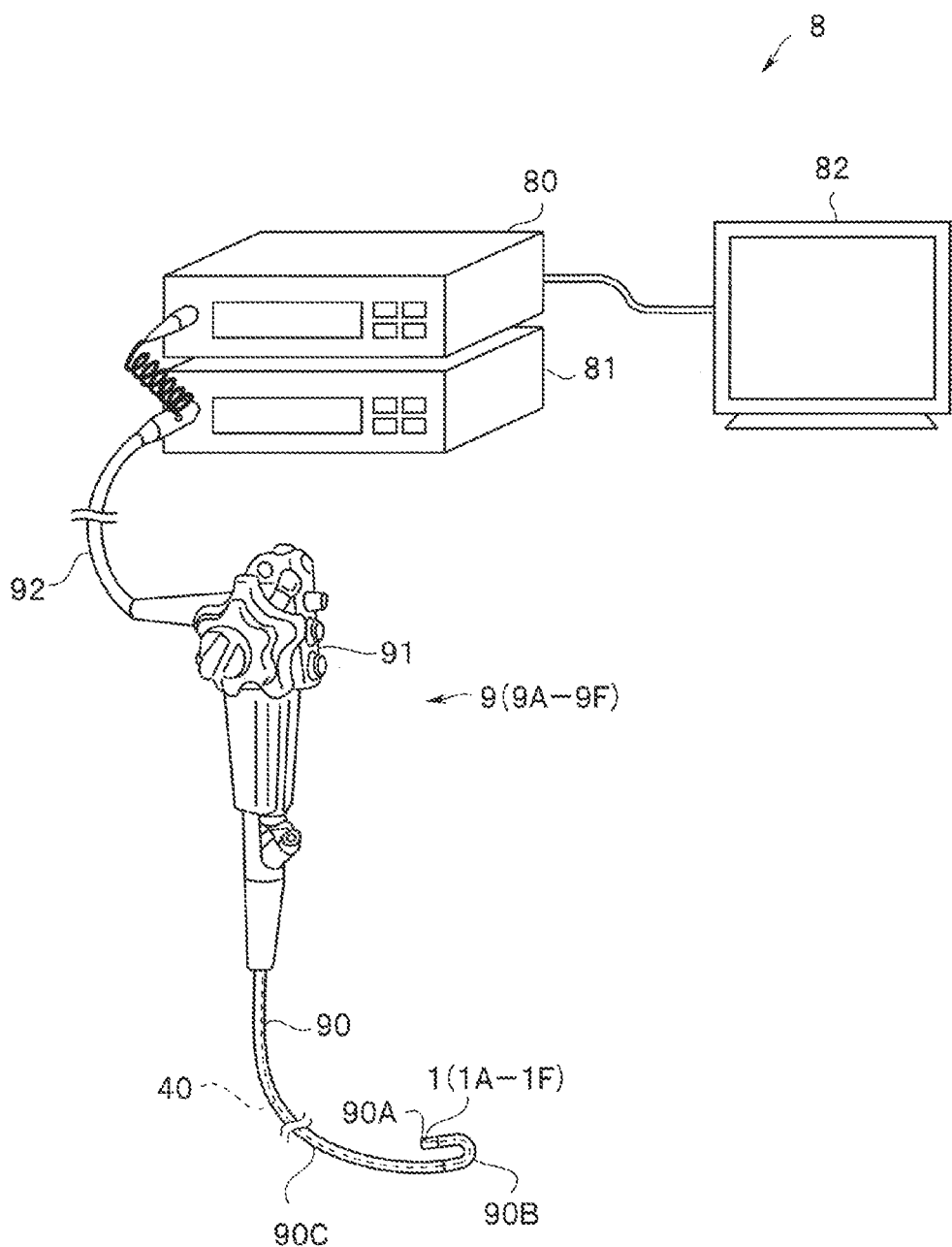
FIG. 1 is a perspective view of an endoscope system including an endoscope of an embodiment.

As shown in FIG. 1, an endoscope system 8 including an endoscope 9 of an embodiment includes the endoscope 9, a processor 80, a light source apparatus 81, and a monitor 82. The endoscope 9 includes an insertion portion 90, an operation portion 91, and a universal cord 92. The insertion portion 90 of the endoscope 9 is inserted into the body cavity of the subject to pick up an in-vivo image of the subject, and to output an image signal.

The insertion portion 90 is formed of a rigid distal end portion 90A, a bending portion 90B, and a flexible portion 90C. An image pickup apparatus for endoscope 1 (hereinafter also referred to as "image pickup apparatus 1") is provided in the distal end portion 90A. The bendable bending portion 90B is continuously formed with the proximal end portion of the distal end portion 90A. The flexible portion 90C is continuously formed with the proximal end portion of the bending portion 90B. The bending portion 90B bends in response to the operation of the operation portion 91. Note that the endoscope 9 may be a rigid endoscope, and may be used as a medical endoscope or an industrial endoscope.

The proximal end portion of the insertion portion 90 of the endoscope 9 is provided with the operation portion 91 having various buttons which operate the endoscope 9.

The light source apparatus 81 includes a white LED, for example. Illumination light emitted from the light source apparatus 81 is guided to the distal end portion 90A through a light guide (not shown in the drawing), thus illuminating the object, the light guide inserted through the universal cord 92 and the insertion portion 90.

The endoscope 9 includes the insertion portion 90, the operation portion 91, and the universal cord 92. Image pickup signals outputted from the image pickup apparatus 1, provided at the distal end portion 90A of the insertion portion 90, are transmitted through an electric cable 40 inserted through the insertion portion 90.

As will be described later, the image pickup apparatus 1 has a short outer dimension in an optical axis direction and hence, a rigid distal end portion 90A of the endoscope 9 has a short length. Therefore, the endoscope 9 is minimally invasive. The image pickup apparatus 1 can be easily manufactured and hence, the endoscope 9 can also be easily manufactured.

<Image Pickup Apparatus for Endoscope>

Figure 2:
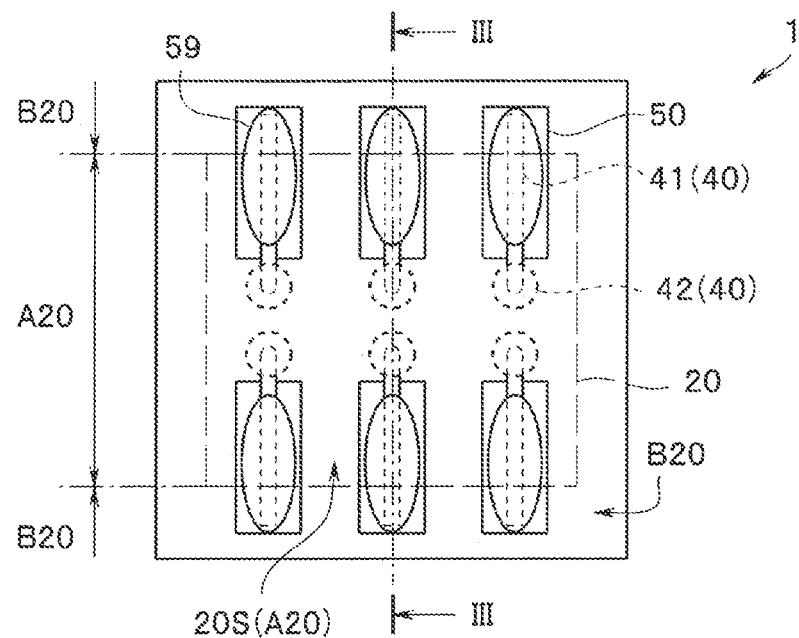
FIG. 2 is a top plan view of an image pickup apparatus of the embodiment.
Figure 3:
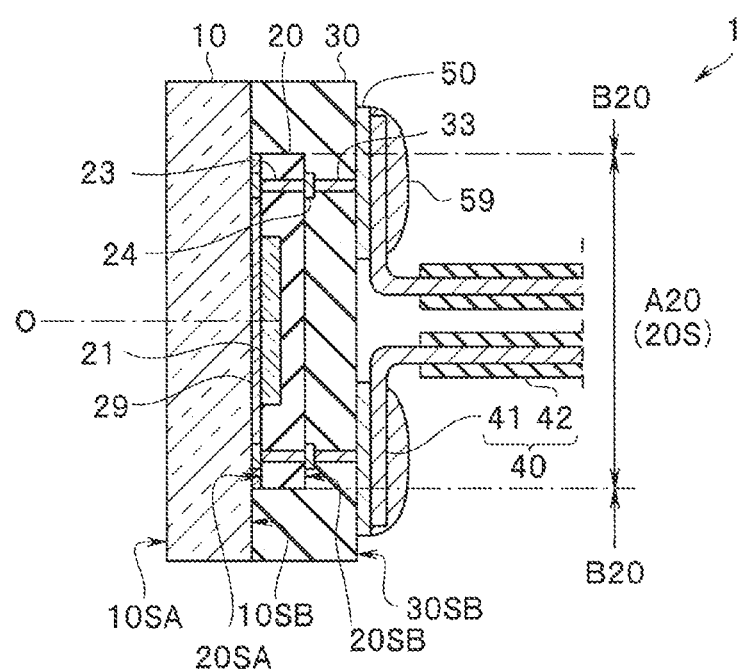
FIG. 3 is a cross-sectional view of the image pickup apparatus of the embodiment taken along line III-III in FIG. 2.

As shown in FIG. 2 and FIG. 3, the image pickup apparatus for endoscope 1 of the embodiment includes a cover glass 10, which is an optical system, an image pickup device 20, which is an image pickup member, a resin member 30, and a plurality of electric cables 40.

In the description made hereinafter, drawings based on the embodiment are schematic views. A relationship between thicknesses and widths of the respective portions, a ratio between thicknesses of the respective portions, and a relative angle between the respective portions, for example, may differ from actual ones. The dimensional relations and the ratio may be different between drawings. Further, the illustration of some constitutional elements and use of reference symbols may be omitted. A direction toward the object is referred to as "forward direction".

The cover glass 10 includes a first main surface 10SA and a second main surface 10SB on a side opposite to the first main surface 10SA. A transparent resin plate or the like may also be used in place of the cover glass 10.

The image pickup device (imager chip) 20 includes a light receiving surface 20SA and a back surface 20SB on a side opposite to the light receiving surface 20SA. The cover glass 10 is caused to adhere to the light receiving surface 20SA by a transparent resin 29. The light receiving surface 20SA is smaller than the main surfaces (the first main surface 10SA, the second main surface 10SB) of the cover glass 10.

The image pickup device 20 has a light receiving region 21 on the light receiving surface 20SA. A plurality of external electrodes connected with the light receiving region 21 are first external electrodes 24 provided on the back surface 20SB. The light receiving region 21 on the light receiving surface 20SA is connected with the first external electrodes 24 on the back surface 20SB through device through wirings 23. The image pickup device 20 may be either one of a front surface irradiation type image sensor or a back surface irradiation type image sensor.

The resin member 30 is provided on the second main surface 10SB of the cover glass 10 to cover the image pickup device 20. The resin member 30 includes a third main surface 30SB which is parallel to the second main surface 10SB, and the outer dimension of the third main surface 30SB is equal to the outer dimension of the second main surface 10SB. A plurality of first bonding electrodes 50 are provided on the third main surface 30SB.

The plurality of first bonding electrodes 50 are respectively connected to the plurality of first external electrodes 24 through a plurality of first through wirings 33 penetrating through the resin member 30.

Each of the plurality of electric cables 40 includes a core wire 41, which is a conductor wire, and a first coating layer 42, which covers the core wire 41. For example, the core wire 41 is bonded to the first bonding electrode 50 using a solder 59. Note that bonding between the core wire 41 and the first bonding electrode 50 is not limited to bonding using a solder, and may be bonding using a conductive resin, for example, provided that the core wire 41 can be electrically connected with the first bonding electrode 50.

In the image pickup apparatus 1, the first bonding electrode 50 also forms a fan-out wiring provided to extend between an inside part A20 and an outside part B20 of an extension space 20S, being an extension of the image pickup device 20 in the optical axis direction. The core wire 41 is bonded to the first bonding electrode 50 having the function of the fan-out wiring.

In other words, the image pickup apparatus 1 includes the first external electrodes 24, the first through wirings 33, the first bonding electrodes 50, and the electric cables 40. The first external electrodes 24 are provided on the back surface 20SB of the image pickup device 20. The first through wirings 33 are connected with the first external electrodes 24, and are provided in the inside part A20 of the extension space 20S, being an extension of the image pickup device 20 in the optical axis direction. Each first bonding electrode 50 is connected with the first external electrode 24 through the first through wiring 33. Further, the first bonding electrode 50 forms the fan-out wiring. Each electric cable 40 is bonded to the first bonding electrode 50.

The first bonding electrode 50 which also functions as the fan-out wiring is provided to extend between the inside part A20 and the outside part B20 of the extension space 20S and hence, the first bonding electrode 50 has an elongated shape and a large area. Therefore, the electric cable 40 can be easily bonded to the first bonding electrode 50.

Each electric cable 40 is directly bonded to the first bonding electrode 50 of the image pickup device 20 without using a wiring board and hence, the image pickup apparatus 1 has a short length in the optical axis direction. Further, the first bonding electrodes 50 are provided on the resin member 30 and hence, stress and heat generated at the time of bonding the electric cable 40 to the first bonding electrode 50 are not directly applied to the image pickup device 20. There is no possibility that the image pickup device 20 is deteriorated by stress and heat and hence, the image pickup apparatus 1 and the endoscope 9 have a high manufacturing yield, high performance, and high reliability.

<Method for Manufacturing Image Pickup Apparatus>

A main part of the image pickup apparatus for endoscope 1 is manufactured by a wafer level method.

Although not shown in the drawing, the image pickup devices 20 are manufactured by cutting an image pickup device wafer. A plurality of light receiving regions 21 are formed on the light receiving surface of the image pickup device wafer by using a known semiconductor manufacturing technique. The first external electrodes 24 are provided on the back surface of the image pickup device wafer, and the first external electrodes 24 are connected with the light receiving regions 21 through the device through wirings 23. The image pickup device wafer may have a peripheral circuit that performs primary processing on an output signal from the light receiving regions 21, or that performs processing on a drive control signal.

Figure 4:
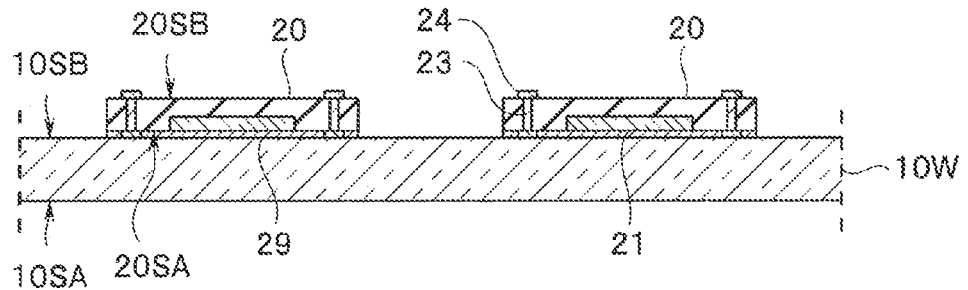
FIG. 4 is a cross-sectional view for describing a method for manufacturing the image pickup apparatus of the embodiment.

As shown in FIG. 4, the light receiving surface 20SA of the plurality of image pickup devices 20 are caused to adhere to the second main surface 10SB of a glass wafer 10W by using the transparent resin 29. The device through wirings 23 are formed in the image pickup device 20 by a method disclosed in Japanese Patent Application Laid-Open Publication No. 2017-103478, for example, after the plurality of image pickup devices 20 are caused to adhere to the glass wafer 10W.

Figure 5:
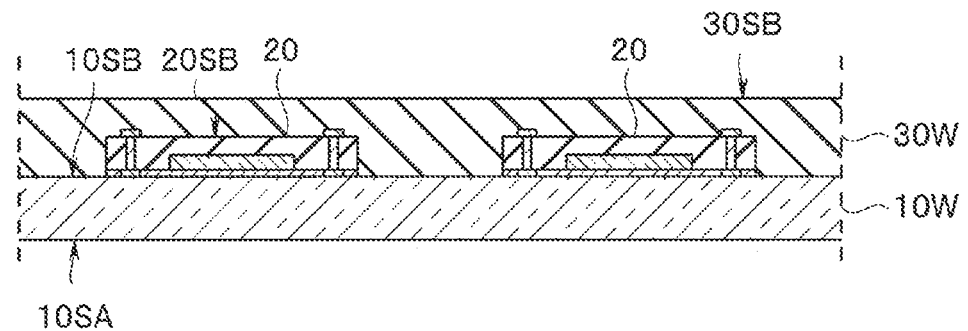
FIG. 5 is a cross-sectional view for describing the method for manufacturing the image pickup apparatus of the embodiment.

Next, as shown in FIG. 5, a resin 30W is provided on the second main surface 10SB of the glass wafer 10W, so that the image pickup devices 20 are covered by the resin 30W. For example, the resin 30W is provided in such a manner that an uncured epoxy resin is applied by coating on the second main surface 10SB, and then curing processing is performed. After the curing processing is performed, the surface (the third main surface 30SB) of the resin 30W may be flattened by polishing or the like. A transfer mold or a laminated film may also be used for forming the resin 30W.

Figure 6:
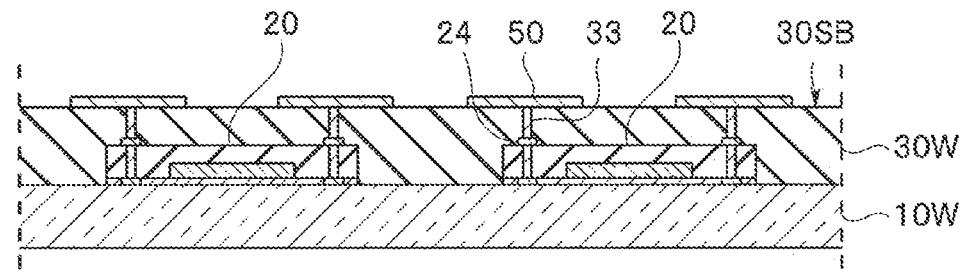
FIG. 6 is a cross-sectional view for describing the method for manufacturing the image pickup apparatus of the embodiment.

As shown in FIG. 6, the plurality of first through wirings 33 penetrating through the resin 30W are provided, and the plurality of first bonding electrodes 50 are provided on the third main surface 30SB. For example, the first through wirings 33 are provided in such a manner that holes are formed in the resin 30W using a laser and, thereafter, the holes are filled with a conductive material. Then, the plurality of first bonding electrodes 50 are provided in such a manner that a conductive film is formed on the third main surface 30SB and, thereafter, patterning is performed.

Figure 7:
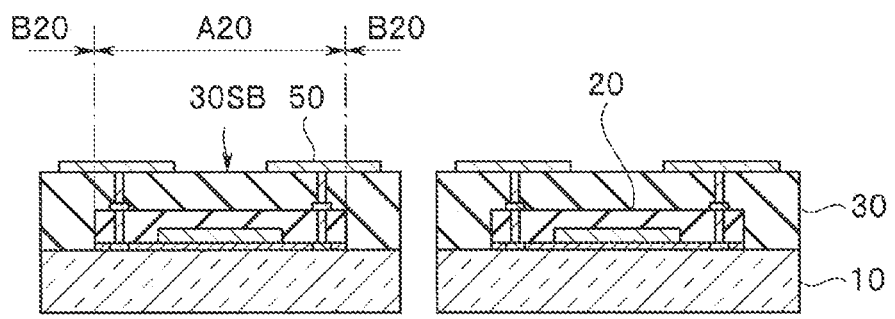
FIG. 7 is a cross-sectional view for describing the method for manufacturing the image pickup apparatus of the embodiment.

By cutting the wafer including the plurality of image pickup devices 20 as shown in FIG. 7, the plurality of image pickup devices 20 are formed, each image pickup device 20 being sealed by the resin member 30, and having the cover glass 10 caused to adhere to the image pickup device 20.

The plurality of image pickup devices 20 are formed by cutting the resin 30W covering the glass wafer 10W and hence, the side surface of the cover glass 10 and the side surface of the resin member 30 have a coplanar cut surface. In other words, the outer dimension of the cover glass 10 and the outer dimension of the resin member 30 are equal to each other.

Although not shown in the drawing, the core wire 41 of the electric cable 40 is bonded to the first bonding electrode 50 by soldering, for example, thus completing the image pickup apparatus 1.

In the image pickup apparatus 1, each first bonding electrode 50 also forms the fan-out wiring provided to extend between the inside part A20 and the outside part B20 of the extension space 20S, being an extension of the image pickup device 20 in the optical axis direction. In other words, the core wire 41 is bonded to the first bonding electrode 50 having the function of the fan-out wiring.

The first bonding electrode 50 which also functions as the fan-out wiring is provided to extend between the inside part A20 and the outside part B20 of the extension space 20S, thus having a large area. The first bonding electrodes 50 are provided on the resin member 30 and hence, stress and heat generated at the time of bonding the electric cable 40 to the first bonding electrode 50 are not directly applied to the image pickup device 20. The core wire 41 can be easily bonded to the first bonding electrode 50 having a large area and hence, the image pickup apparatus 1 can be easily manufactured, and an endoscope including the image pickup apparatus 1 can also be easily manufactured.

<Modifications>

The image pickup apparatuses for endoscope 1A to 1F (hereinafter also respectively referred to as "image pickup apparatus 1A" to "image pickup apparatus 1F") of the modifications 1 to 6 are similar to the image pickup apparatus for endoscope 1, and have advantageous effects equal to the advantageous effects of the image pickup apparatus for endoscope 1. Accordingly, constitutional elements having the same function are given the same reference symbols, and the repeated description will be omitted.

<Modification 1>

Figure 8:
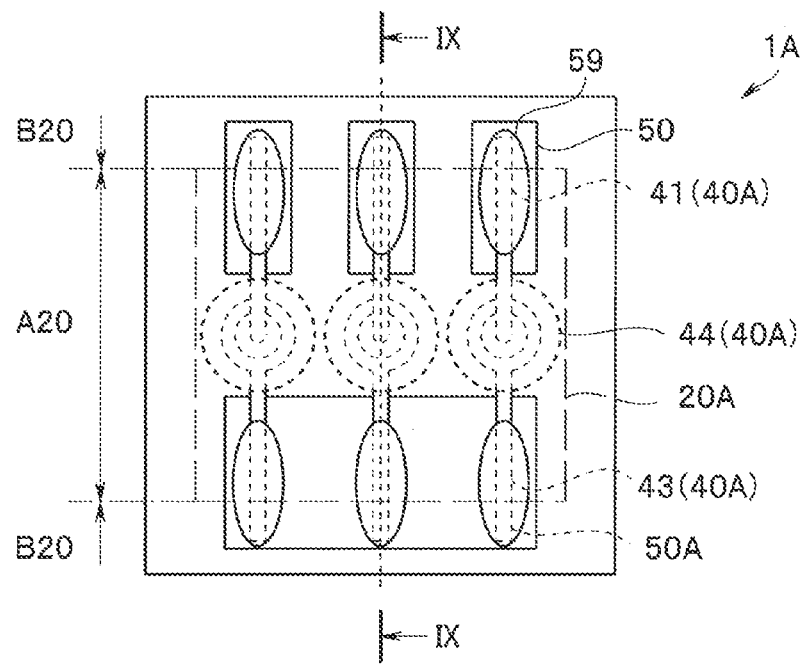
FIG. 8 is a top plan view of an image pickup apparatus of a modification 1.
Figure 9:
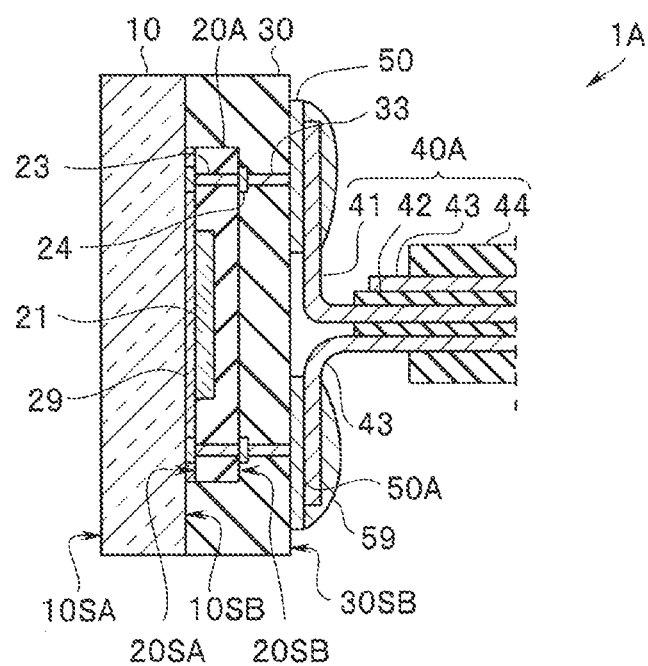
FIG. 9 is a cross-sectional view of the image pickup apparatus of the modification 1 taken along line IX-IX in FIG. 8.

In the image pickup apparatus 1A of the modification shown in FIG. 8 and FIG. 9, the electric cable is a shielded cable 40A. The shielded cable 40A includes the core wire 41, which is a conductor wire, the first coating layer 42, which covers the core wire 41, a shielding wire 43 which covers the first coating layer 42, and a second coating layer 44, which covers the shielding wire 43.

A first bonding electrode 50A connected to a ground potential electrode in the light receiving region 21 of an image pickup device 20A is a common electrode bonded to the shielding wires 43 of three shielded cables 40A. Each first bonding electrode 50 is bonded to the core wire 41 of the shielded cable 40A.

The image pickup apparatus 1A which includes the shielded cables 40A each including the shielding wire 43 is superior in noise resistance to the image pickup apparatus 1.

<Modification 2>

Figure 10:
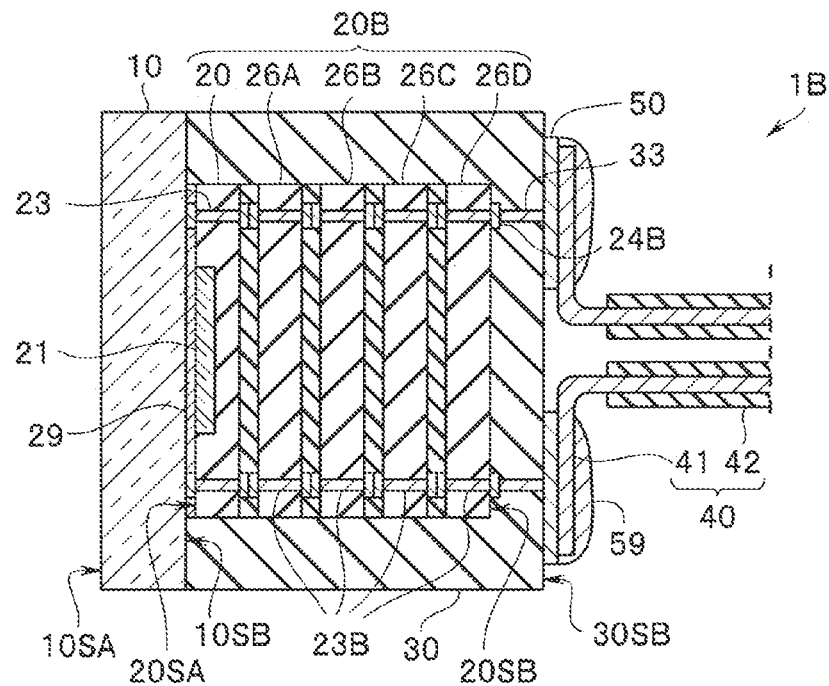
FIG. 10 is a cross-sectional view of an image pickup apparatus of a modification 2.

In the image pickup apparatus 1B of the modification shown in FIG. 10, the image pickup member is a laminated device 20B in which a plurality of semiconductor devices 20, 26A to 26D including the image pickup device 20 are laminated.

The semiconductor devices 26A to 26D perform primary processing on an image pickup signal outputted from the image pickup device 20, or perform processing on a control signal for controlling the image pickup device 20. The semiconductor devices 26A to 26D include function units, such as an AD conversion circuit, a memory, a transmission output circuit, a filter circuit, a thin film capacitor, a thin film resistor, or a thin film inductor. The number of devices included in the laminated device 20B, including the image pickup device 20, is 2 or more and 10 or less, for example.

In the image pickup apparatus 1B in which the image pickup member is the laminated device 20B, an image pickup signal outputted from the image pickup device 20 is processed through a transmission path shorter than the transmission path of the image pickup apparatus 1 and hence, the signal is little deteriorated.

<Modification 3>

Figure 11:
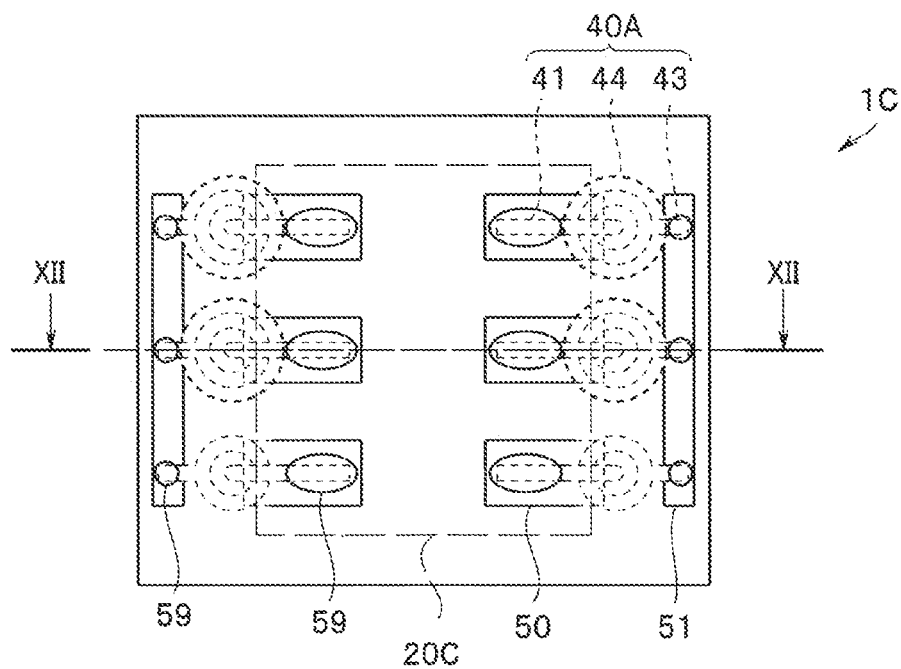
FIG. 11 is a top plan view of an image pickup apparatus of a modification 3.
Figure 12:
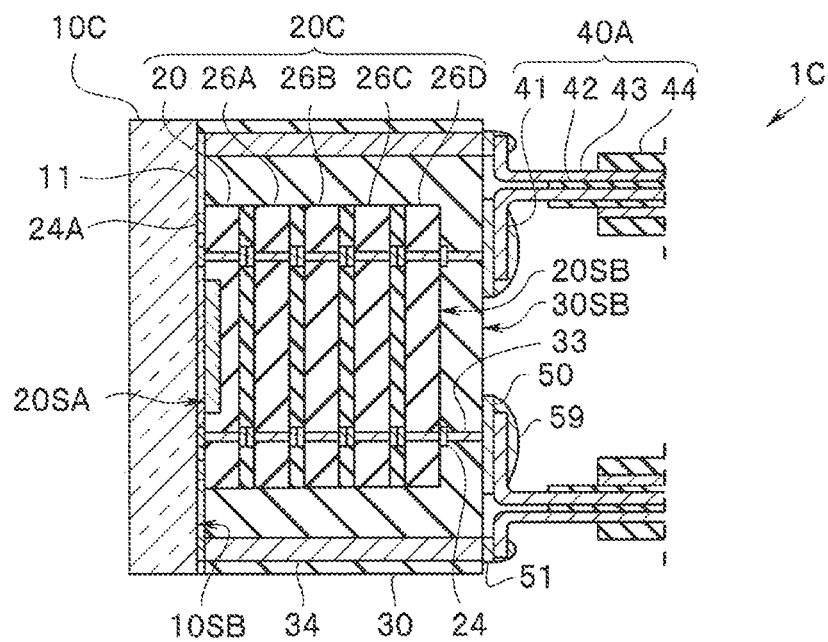
FIG. 12 is a cross-sectional view of the image pickup apparatus of the modification 3 taken along line XII-XII in FIG. 11.

In the image pickup apparatus 1C of the modification shown in FIG. 11 and FIG. 12, the image pickup member is a stacked device 20C in which a plurality of semiconductor devices 20, 26A to 26D including the image pickup device 20 are laminated, and the electric cable is the shielded cable 40A.

Figure 13:
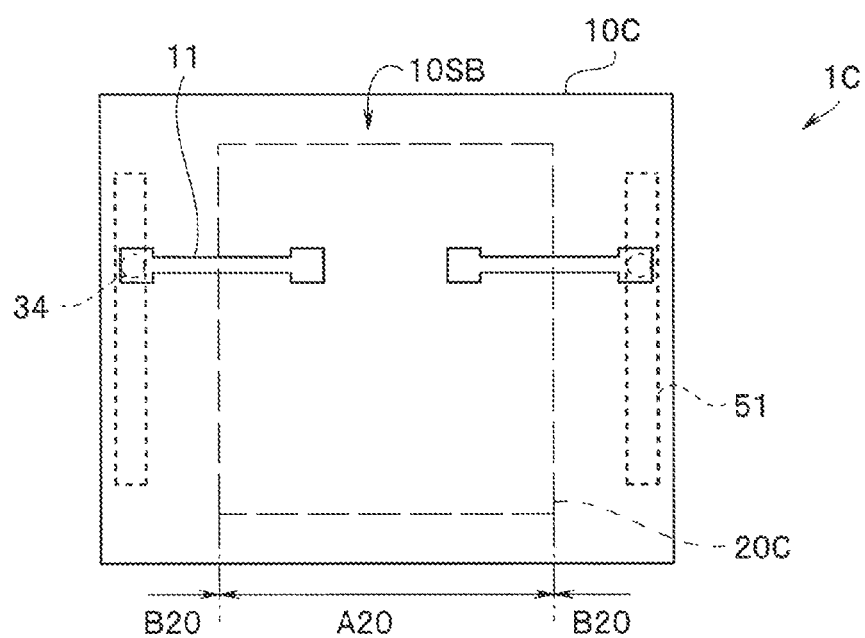
FIG. 13 is a plan view of a cover glass of the image pickup apparatus of the modification 3.

Further, as shown in FIG. 12, at least one external electrode of the stacked device 20C includes the first external electrode 24 and a second external electrode 24A. The second external electrode 24A is provided on the light receiving surface 20SA. As shown in FIG. 13, fan-out wirings (second fan-out wirings) 11 are provided on the second main surface 10SB of a cover glass 10C such that each fan-out wiring 11 extends between the inside part A20 and the outside part B20 of the extension space 20S, being an extension of the stacked device 20C in the optical axis direction. Further, through wirings penetrating through the resin member 30 of the image pickup apparatus 1C include at least one first through wiring 33 and at least one second through wiring 34.

The bonding electrodes on the third main surface 30SB of the resin member 30 include at least one first bonding electrode 50 and at least one second bonding electrode 51. The second bonding electrode 51 is connected with the second external electrode 24A through the fan-out wiring 11 and the second through wiring 34. The second through wiring 34 is provided in the outside part B20 of the extension space 20S, being an extension of the stacked device 20C in the optical axis direction.

The second bonding electrode 51 is a common electrode for the shielding wires 43 of a plurality of shielded cables 40A. The second bonding electrode 51 is provided in the outside part B20 of the extension space 20S, being an extension of the stacked device 20C in the optical axis direction.

The image pickup apparatus 1C has the advantageous effects of the image pickup apparatuses 1, 1A, 1B. In the case where the through wirings are provided in the semiconductor device, when the number of through wirings is large or the diameter of the through wirings is large, a region for forming a circuit is reduced. In the image pickup apparatus 1C, signals can also be transmitted through the fan-out wiring 11 provided on the second main surface 10SB of the cover glass 10C, the second through wiring 34, and the second bonding electrode 51. Accordingly, the image pickup apparatus 1C can further improve yield, further reduce costs, and further improve design freedom compared with the image pickup apparatus 1 and the like.

The second external electrode 24A connected with the fan-out wiring 11 is not limited to the ground potential electrode. For example, it is preferable that a synchronizing signal or a power signal (drive signal) which is directly inputted to the stacked device 20C should be transmitted through the fan-out wiring 11 (the second through wiring 34) without passing through the semiconductor devices 26A to 26D. Particularly, the width of the second through wiring 34, which is provided in the resin member 30, can be easily increased compared with the first through wiring 33 provided in the semiconductor device. Therefore, it is particularly preferable to use the second through wiring 34 as a wiring which transmits a drive signal which has large power.

The second bonding electrode 51 may be provided to extend from the outside part B20 to the inside part A20 of the extension space 20S, being an extension of the stacked device 20C in the optical axis direction.

In other words, in the image pickup apparatus 1C, the external electrodes include the first external electrode 24 and the second external electrode 24A. The through wirings include the first through wiring 33 and the second through wiring 34. The bonding electrodes include the first bonding electrode 50 and the second bonding electrode 51.

<Modification 4>

Figure 14:
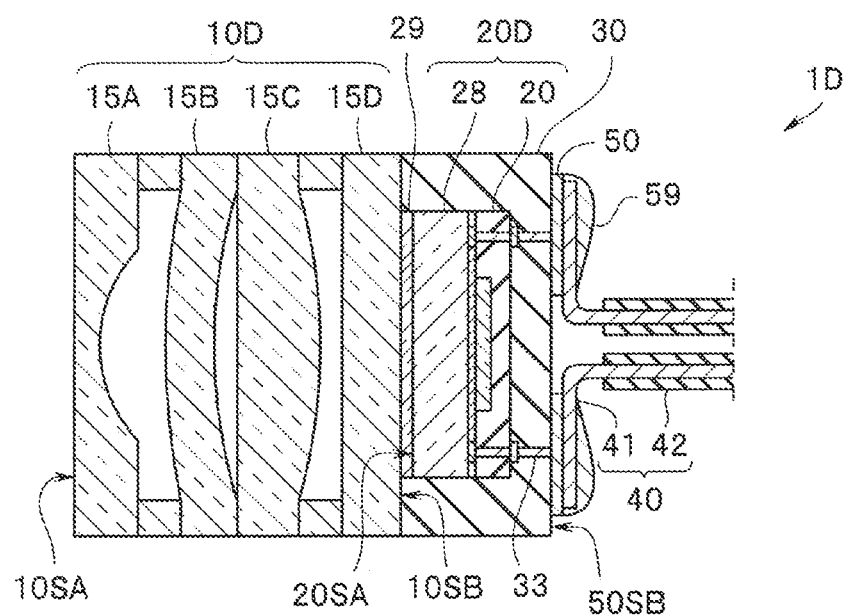
FIG. 14 is a cross-sectional view of an image pickup apparatus of a modification 4.

In the image pickup apparatus 1D of the modification shown in FIG. 14, the optical system is a lens unit 10D including a plurality of optical members 15A to 15D. In the image pickup apparatus 1D, each image pickup member 20D includes a cover glass 28 and the image pickup device 20.

In the image pickup member 20D, the surface of the cover glass 28 on a side opposite to the surface of the cover glass 28 caused to adhere to the image pickup device 20 forms the light receiving surface 20SA.

The optical members 15A to 15C are lenses, and the optical member 15D is a filter. The lens unit may include other optical members, such as an aperture, and the number of optical members of the lens unit is designed according to the specifications.

Each lens unit 10D is formed by cutting a laminated optical wafer in which a plurality of optical wafers including the optical members 15A to 15D are laminated, for example. In other words, the plurality of image pickup members 20D are caused to adhere to the laminated optical wafer and, thereafter, the resin member 30 is provided. Then, the first through wirings 33 and the first bonding electrodes 50 are provided and, thereafter, cutting processing is performed.

The image pickup apparatus 1D includes the lens unit 10D, thus having high performance. Further, the lens unit 10D is formed by a wafer level method and hence, the lens unit 10D can be manufactured more easily than the image pickup apparatus 1 or the like in which the lens unit is provided in a subsequent step.

<Modification 5>

Figure 15:
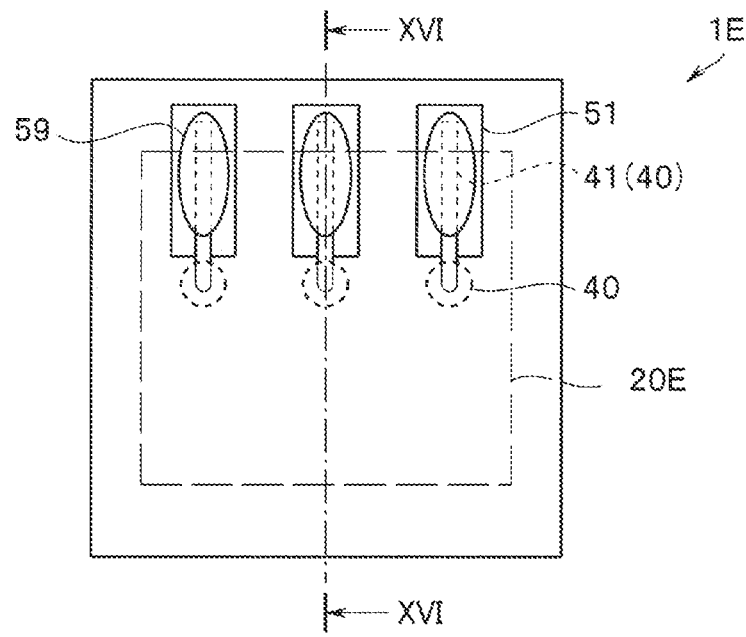
FIG. 15 is a top plan view of an image pickup apparatus of a modification 5.
Figure 16:
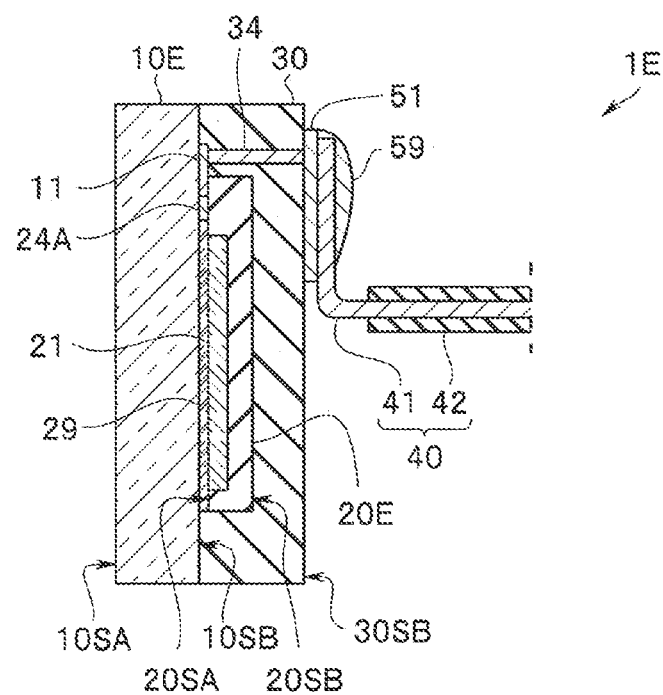
FIG. 16 is a cross-sectional view of the image pickup apparatus of the modification 5 taken along line XVI-XVI in FIG. 15.

In the image pickup apparatus 1E of the modification shown in FIG. 15 and FIG. 16, all external electrodes are the second external electrodes 24A provided on the light receiving surface 20SA. The second bonding electrode 51 is provided to extend from the outside part B20 to the inside part A20 of the extension space 20S, being an extension of the stacked device 20C in the optical axis direction. The fan-out wiring 11 is provided on the second main surface 10SB of a cover glass 10E, the fan-out wiring 11 being connected with the second external electrode 24A.

Each of all through wirings is the second through wiring 34 which connects the second external electrode 24A on the light receiving surface 20SA and the second bonding electrode 51. The second external electrode 24A is connected with the second bonding electrode 51 on the third main surface 30SB through the fan-out wiring 11 and the second through wiring 34 penetrating through the resin member 30.

An image pickup device 20E having no device through wiring can be easily manufactured and hence, the image pickup apparatus 1E can be easily manufactured.

<Modification 6>

Figure 17:
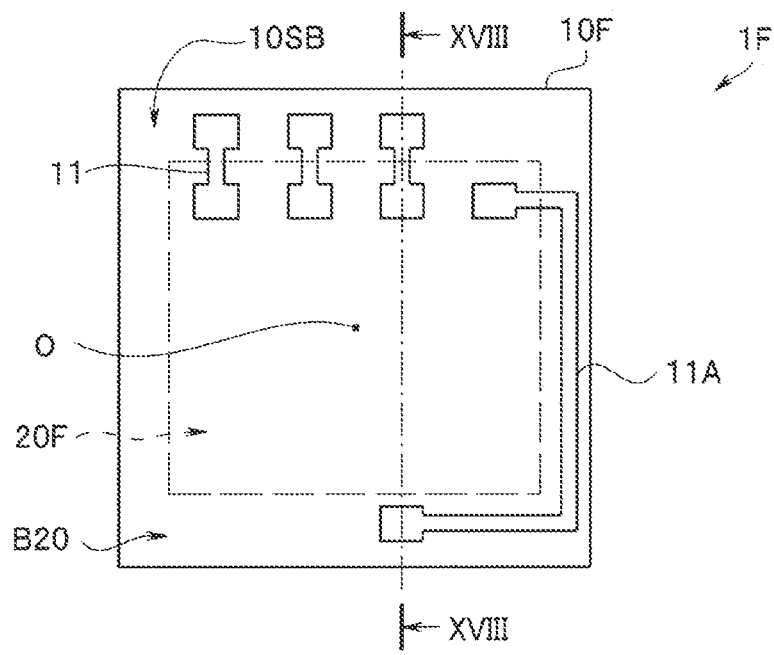
FIG. 17 is a plan view of a cover glass of an image pickup apparatus of a modification 6.
Figure 18:
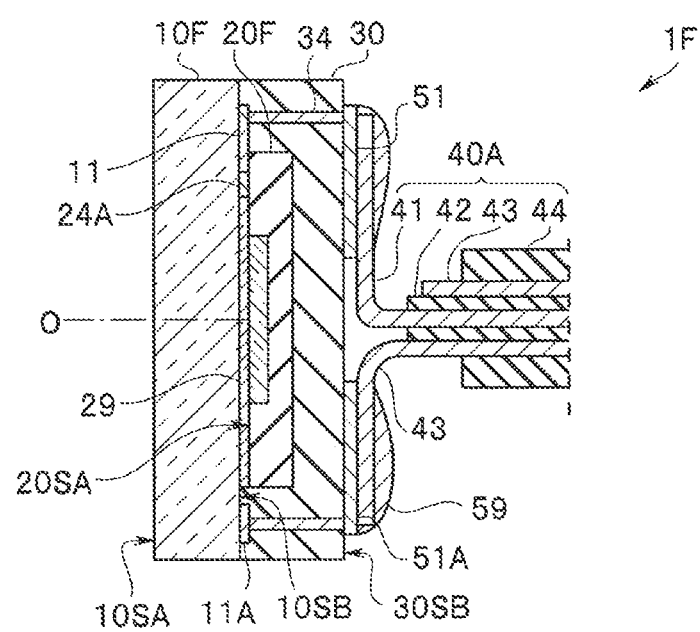
FIG. 18 is a cross-sectional view of the image pickup apparatus of the modification 6 taken along line XVIII-XVIII in FIG. 17.

In the image pickup apparatus 1F of the modification shown in FIG. 17 and FIG. 18, in the same manner as the image pickup apparatus 1E, all external electrodes are the second external electrodes 24A provided on the light receiving surface 20SA of an image pickup device 20F, and all through wirings are the second through wirings 34 extending in the outside part B20 of the extension space 20S, being an extension of the image pickup device 20F in the optical axis direction. In the image pickup apparatus 1F, the electric cable is the shielded cable 40A.

On the second main surface 10SB of a cover glass 10F, one of the fan-out wirings 11 connected with the second external electrode 24A is a ground potential wiring 11A. The ground potential wiring 11A is provided to extend to one outer peripheral region on a side opposite to another outer peripheral region with respect to the optical axis O, where other fan-out wirings 11 are provided.

The second bonding electrode 51 for transmitting a signal and a second bonding electrode 51A at the ground potential are respectively provided in the outer peripheral regions on both sides of the optical axis O. The core wire 41 of the shielded cable 40A is bonded to the second bonding electrode 51.

The image pickup apparatus 1F has the advantageous effects of the image pickup apparatus 1E, and signal is little deteriorated in the image pickup apparatus 1F. Further, the second bonding electrode 51 and the second bonding electrode 51A are provided in the regions separated from each other and hence, the core wire 41 and the shielding wire 43 can be easily bonded.

Needless to say, endoscopes 9A to 9F including the image pickup apparatuses 1A to 1F have the advantageous effects of the image pickup apparatuses 1A to 1F in addition to the advantageous effects of the endoscope 9.

The present invention is not limited to the above-mentioned embodiment and the like, and various changes or modifications, for example, are conceivable without departing from the gist of the present invention.

What is claimed is:

1. An image pickup apparatus for endoscope comprising:
   an optical system including a first main surface and a second main surface on a side opposite to the first main surface;
   a resin member provided on the second main surface, and having a third main surface which is parallel to the second main surface, an outer dimension of the third main surface being equal to an outer dimension of the second main surface;
   an image pickup member including a light receiving surface and a back surface on a side opposite to the light receiving surface, the light receiving surface having a light receiving region, the light receiving surface being caused to adhere to the second main surface by a transparent resin, the back surface being covered by the resin member, the light receiving surface being smaller than the second main surface, the image pickup member including a plurality of external electrodes including a first external electrode provided on the back surface;
   a transparent adhesive adhering the light receiving surface to the second main surface;
   a plurality of fan-out wirings, each of which is provided to extend from within a projection of the image pickup member in an optical axis direction to outside the projection of the image pickup member;
   a plurality of through wirings including a first through wiring, the first through wiring penetrating through the resin member, the first through wiring connected with the first external electrode, and the first through wiring provided within the projection of the image pickup member;
   a plurality of bonding electrodes including a first bonding electrode provided on the third main surface, the first bonding electrode connected with the first external electrode through the first through wiring, and the first bonding electrode forming a fan-out wiring of the plurality of fan-out wirings; and
   a plurality of electric cables bonded to the plurality of bonding electrodes.

2. The image pickup apparatus for endoscope according to claim 1, wherein
   the plurality of external electrodes include a second external electrode provided on the light receiving surface,
   the plurality of fan-out wirings include a second fan-out wiring provided on the second main surface,
   the plurality of through wirings include a second through wiring connected with the second fan-out wiring and provided outside the projection of the image pickup member, and
   the plurality of bonding electrodes include a second bonding electrode connected with the second external electrode through the second fan-out wiring and the second through wiring.

3. The image pickup apparatus for endoscope according to claim 1, wherein
   the electric cable is a shielded cable including a core wire and a shielding wire, and
   the core wire is bonded to any one of the plurality of bonding electrodes, and the shielding wire is bonded to any other one of the plurality of bonding electrodes.

4. The image pickup apparatus for endoscope according to claim 1, wherein the image pickup member is an image pickup device.

5. The image pickup apparatus for endoscope according to claim 1, wherein the image pickup member comprises a plurality of semiconductor devices including an image pickup device laminated in the optical axis direction.

6. The image pickup apparatus for endoscope according to claim 1, wherein the optical system is a lens unit in which a plurality of optical members are laminated in the optical axis direction.

7. An endoscope comprising:
   an insertion portion;
   an image pickup apparatus provided at a distal end portion of the insertion portion, wherein the image pickup apparatus comprises:
- an optical system including a first main surface and a second main surface on a side opposite to the first main surface;
- a resin member provided on the second main surface, and having a third main surface which is parallel to the second main surface, an outer dimension of the third main surface being equal to an outer dimension of the second main surface;
- an image pickup member including a light receiving surface and a back surface on a side opposite to the light receiving surface, the light receiving surface having a light receiving region, the light receiving surface being caused to adhere to the second main surface by a transparent resin, the back surface being covered by the resin member, the light receiving surface being smaller than the second main surface, the image pickup member including a plurality of external electrodes including a first external electrode provided on the back surface;
- a transparent adhesive adhering the light receiving surface to the second main surface;
- a plurality of fan-out wirings, each of which is provided to extend from within a projection of the image pickup member in an optical axis direction to outside the projection of the image pickup member;
- a plurality of through wirings including a first through wiring, the first through wiring penetrating through the resin member, the first through wiring connected with the first external electrode, and the first through wiring provided within the projection of the image pickup member; and
- a plurality of bonding electrodes including a first bonding electrode provided on the third main surface, the first bonding electrode connected with the first external electrode through the first through wiring, and the first bonding electrode forming a fan-out wiring of the plurality of fan-out wirings; and
- a plurality of electric cables bonded to the plurality of bonding electrodes.

8. An image pickup apparatus for endoscope comprising:
one or more semiconductor devices including a light receiving surface and a back surface on a side opposite to the light receiving surface, the light receiving surface including an image sensor having a light receiving region, the one or more semiconductor devices including a plurality of external electrodes including a first external electrode provided on the back surface and a second external electrode provided on the light receiving surface, the second external electrode being connected to the image sensor, the second external electrode provided outside of the light receiving region in an optical axis direction;
a resin member having a first main surface, an outer dimension of the resin member being larger than an outer dimension of the back surface, the resin member at least covering the back surface and an outer peripheral side surface of the one or more semiconductor devices;
a plurality of bonding electrodes including a first bonding electrode provided on the first main surface, the first bonding electrode extending from within a projection of the one or more semiconductor devices in an optical axis direction to outside the projection of the one or more semiconductor devices; and
a plurality of through wirings including a first through wiring penetrating through the one or more semiconductor devices and the resin member, electrically connecting the second external electrode to the first bonding electrode.

9. The image pickup apparatus according to claim 8, further comprising an optical system disposed distally relative to the light receiving surface in the optical axis direction.

10. The image pickup apparatus according to claim 9, wherein the optical system includes a transparent plate, an outer dimension of the resin member is equal to an outer dimension of the transparent plate.

11. The image pickup apparatus according to claim 9, wherein the optical system includes a transparent plate, an outer dimension of transparent plate is equal to an outer dimension of the one or more semiconductor devices.

12. The image pickup apparatus according to claim 11, wherein the resin member further covers an outer peripheral side surface of the transparent plate.

13. The image pickup apparatus according to claim 9, wherein the optical system comprises a transparent plate and one or more optical lenses.

14. The image pickup apparatus according to claim 13, further comprising an optical filter disposed between the one or more lenses and the transparent plate.

15. The image pickup apparatus according to claim 8, wherein the one or more semiconductor devices comprise a plurality of semiconductor devices laminated in the optical axis direction, the light receiving surface being a distal-most surface of the plurality of semiconductor devices in the optical axis direction.

16. The image pickup apparatus according to claim 8, wherein the first bonding electrode comprising a plurality of first electrodes, each extending from within the projection to outside the projection.

17. The image pickup apparatus according to claim 16, wherein the plurality of first electrodes each extending in a same direction from within the projection to outside the projection.

18. The image pickup apparatus according to claim 16, wherein the plurality of first electrodes including:
- a first subset of the plurality of first electrodes each extending in a first direction from within the projection to outside the projection; and
- a second subset of the plurality of first electrodes each extending in a second direction, different from the first direction, from within the projection to outside the projection.

19. The image pickup apparatus according to claim 8, wherein:
- the light receiving surface further having a third electrode and a wiring connecting the third electrode to the image sensor, the third electrode being outside the projection of the one or more semiconductor devices in an optical axis direction;
- a second bonding electrode electrically isolated from the first bonding electrode, the second bonding electrode disposed on the first main surface; and
- a second through wiring disposed in the resin member connecting the third electrode to the second bonding electrode.

20. An endoscope comprising:
an insertion section configured to be inserted into a subject; and
the image pickup apparatus according to claim 8 disposed in the insertion section.

* * * * *